United States Patent [19]

Lemos

[11] 3,979,829

[45] Sept. 14, 1976

[54] APPARATUS FOR PREPARING A TOOTH STUMP FOR A CROWN

[75] Inventor: Albano Lemos, Winter Park, Fla.

[73] Assignee: Bell Bur, Inc., Winter Park, Fla.

[22] Filed: Nov. 26, 1975

[21] Appl. No.: 635,609

[52] U.S. Cl. ................................................ 32/49
[51] Int. Cl.² ........................................ A61C 3/02
[58] Field of Search ......................... 32/48, 49, 12

[56] References Cited
UNITED STATES PATENTS

| 1,216,683 | 2/1917 | Greenfield | 32/48 |
| 2,707,329 | 5/1955 | Costoff | 32/48 |

*Primary Examiner*—Robert Peshock
*Attorney, Agent, or Firm*—Roger L. Martin

[57] ABSTRACT

A rotary cutting tool for the reception in a dental drill and use in preparing a tooth stump for the mounting of a tooth crown has a frustoconical cavity and a frustoconical lateral exterior surface. The exterior surface shape facilitates manipulation of the tool by the dentist and the interior shape is covered with abrasive matter that, in use of the tool, serves to shape both the top and the lateral surfaces of the tooth stump spike. At the base of the tool, an annular, abrasive coated surface is provided to shape the tooth stump and provide a ledge in those situations where the spike is to receive a full crown. Adjacent the annular surface, the lateral exterior surface may be coated with water repellent material that serves to protect adjacent teeth from damage and to also minimize gum damage when gum penetration occurs. Cooling of the work piece with water or other fluids is facilitated by the use of lateral wall passages which are inclined at the trailing edges for the contemplated rotational movement of the tool so that encountered water particles are deflected into the cavity and onto the work surface.

15 Claims, 7 Drawing Figures

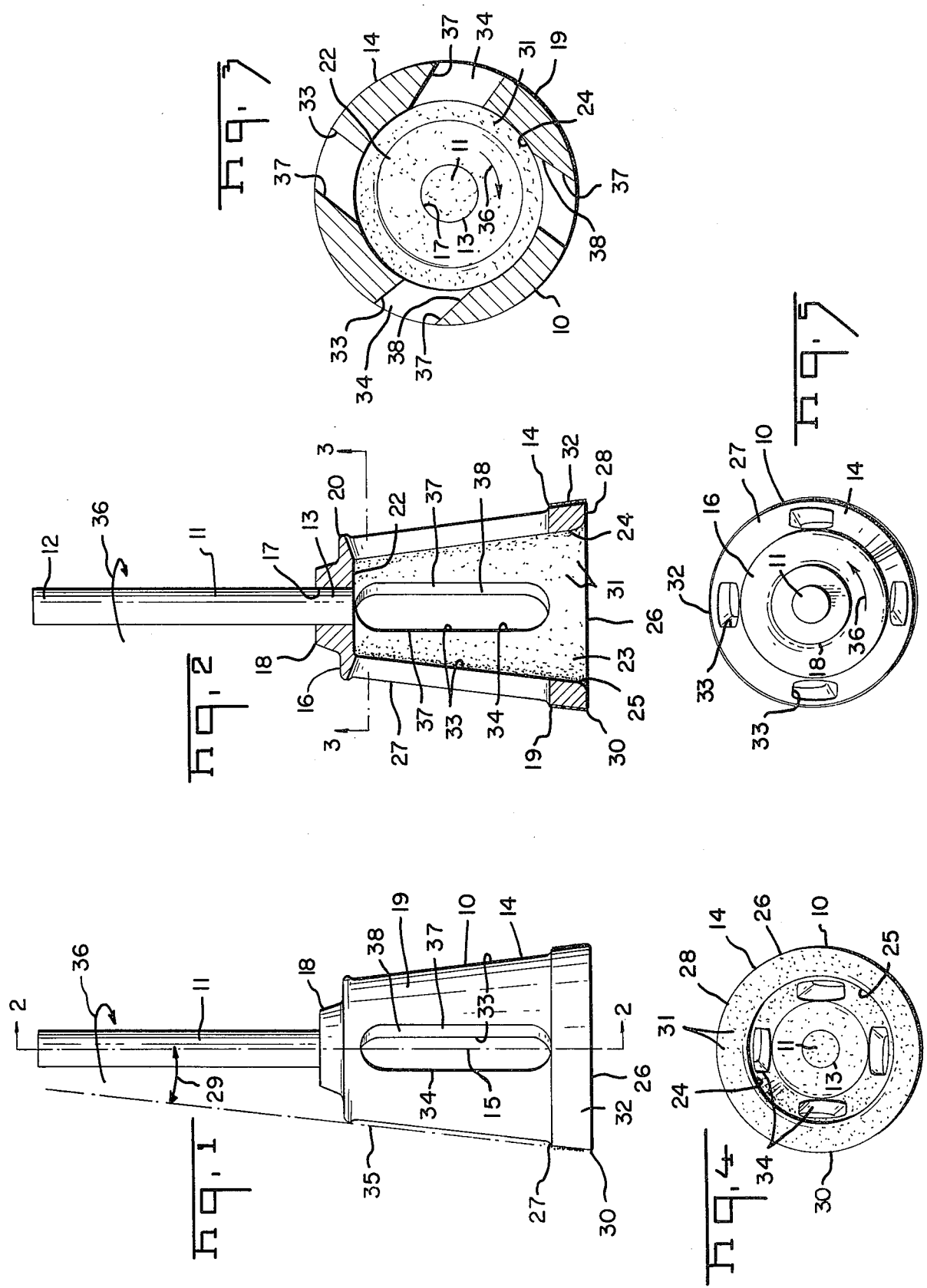

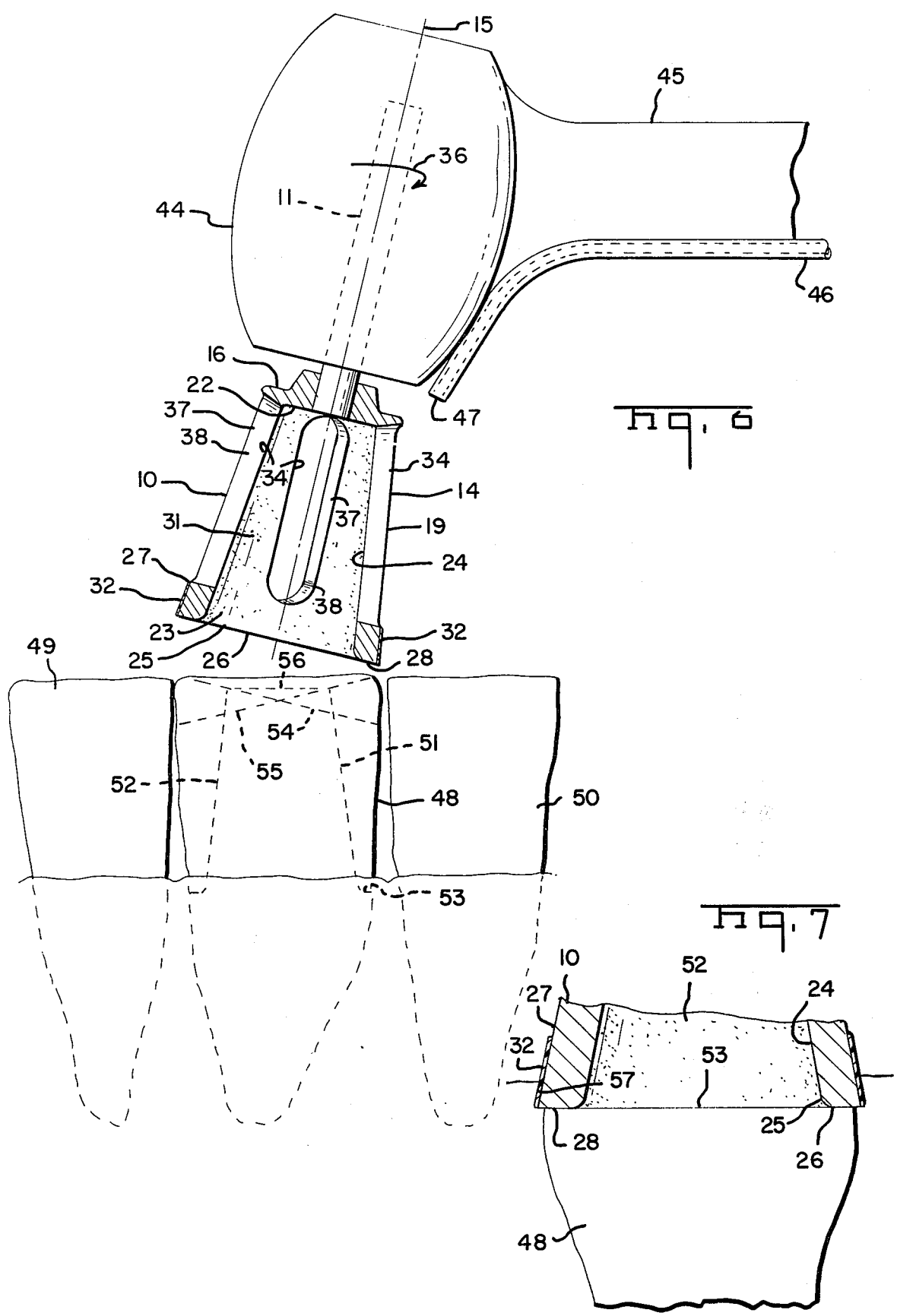

APPARATUS FOR PREPARING A TOOTH STUMP FOR A CROWN

BACKGROUND OF THE INVENTION

The normal method used by dentists to prepare a tooth for the reception of a crown involves the cutting down of the tooth to provide a generally conical spike on the tooth stump. If the crown to be mounted on the spike is a full crown, the tooth is cut at the base of the spike to provide a ledge on which the base of the crown rests when it is mounted on the spike. In practice, this ledge is cut below the gum line with some ensuing damage to the gum tissue so that when the gum recovers from the lesions it covers the parting line between the crown and tooth stump and provides a natural barrier to the entrance of bacteria, mouth secretions, and food particles to the space between the tooth stump and crown.

The cutting process is usually done by the dentist through the use of several different types of abrasive cutting tools and the ultimate success or failure of the work depends much on the skill of the dentist in forming the ledge and spike for the reception of the crown. The crowns are made from impressions of the stump and if, in the process of preparing the stump, the dentist has made undercuts in the spike area, it not infrequently happens that the prepared crown fails to properly fit on the spike and the base of the crown inadequately seats against the ledge of the tooth stump. Under such circumstances the gum frequently fails to cover the parting line as it recovers from the lesions and this, of course, provides an exposed area where food particles, bacteria, and mouth secretions can seep into the space between the crown and tooth stump.

Attempts have been made to design a cutting tool that would remove much of the dental skill factor required to obtain an undercut free spike during the preparation of the tooth stump. Such attempts have usually centered around the use of a hollow cutting tool for shaping the lateral side wall of the spike. However, such attempts have left the dentist with the need to use other cutting tools in order to shape the apex area of the spike and to shape the ledge at the base of the spike when a full crown is contemplated. The need for using several different types of cutting tools is, of course, time consuming to the dentist and it also gives rise to added patient discomfort. There is, accordingly, a need in the dental profession for a single tool that can be used to not only shape the crown and lateral wall areas of the spike but also the below gum line ledge desired for mounting full crowns.

Several practical problems have been encountered in seeking a cutting tool of the type contemplated. For one, many dental patients have overcrowded teeth situations. This detracts from the use of hollow cutting tools because their sizes gives rise to damage to the enamel of adjacent teeth.

Yet another problem which has been encountered is that of dissipating heat which is generated through the use of such cutting tools. The abrading surfaces which are encountered in such spike shaping tools are vastly greater than the more conventional cutting tool attachments for dental drills. This fact, coupled with the high speed drilling equipment that is now conventionally found in the dental trade results in the generating of a large amount of heat with the resulting discomfort to the patient. Furthermore, the hollow nature of the cutting tools and the high speeds involved make it difficult to flood the work area with cooling water and air in accord with conventional procedures. Furthermore, the effective dissipation of generated heat without interfering with the dentist's view of the work area and his ability to adequately manipulate the cutting tool is of major concern.

BRIEF SUMMARY OF THE INVENTION

The invention relates to a dental cutting tool and associated apparatus for use in preparing tooth stumps for the reception of crowns and more particularly for use in the preparation of such tooth stumps without the need for resorting to other cutting tools to accomplish the objective.

In accord with certain aspects of the invention, the inventor provides a cutting tool with a frustoconically shaped, hollow body member which, because of the exterior body shape, can be readily manipulated by the dentist in the oral cavity area so as to avoid damage to teeth adjacent the tooth stump being prepared. The cavity area of the body conforms to that of the desired tooth stump spike and is coated with abrasive matter that facilitates not only the shaping of the lateral wall of the spike but also of the crown or upper area of the tooth spikes. To facilitate the shaping of the ledge area, the inventor provides an annular exterior abrasion surface that surrounds the cavity opening at the base of the body member. In the lateral wall area adjacent this annular surface the inventor also provides a coating of water repellent material that serves to protect the enamel of adjacent teeth during use of the tool and which also serves to minimize damage to the gums as the below gum line ledge on the tooth stump is being formed.

In accord with other aspects of the invention, it has also been found that through the use of appropriately positioned apertures in the wall of the body and which are provided with an inclined trailing edge fluids can be projected into the aperture and then deflected by the edge into the cavity area. The work surface of the tooth stump can accordingly be flooded with water in order to dissipate the generated heat, and this can be done without the use of shields and other bulky equipment heretofore thought necessary in order to adequately cool the stump being prepared.

A general object of the invention is to provide an improved hollow cutting tool for preparing a tooth stump for the reception of a crown. One particular object is to provide a tool of the kind contemplated and which, without the need for additional cutting tools, can be used by the dentist to both shape the spike and the ledge of a tooth stump being prepared for reception of a full crown. Yet another objective of the invention is to provide a tool of the kind contemplated and which can be used to shape a tooth stump for the reception of a crown without causing undo damage to teeth adjacent the stump. Still another objective of the invention is to provide improvements in hollow cutting tools and which facilitate the distribution of cooling water into the cavity area of the hollow tool. Yet another object is to provide an improved tool for cutting a below gum line ledge in a tooth stump without undo damage to the gum.

BRIEF DESCRIPTION OF THE DRAWINGS

The novel features which are believed to be characteristic of this invention are set forth with particularity in the appended claims. The invention, itself, however, both as to its organization and method of operation, together with further objects and advantages thereof, may best be understood by reference to the following description taken in connection with the accompanying drawings, in which:

FIG. 1 is an enlarged side elevational view of a hollow cutting tool embodying the principles of the invention;

FIG. 2 is a longitudinal sectional view of the tool as seen along the Lines 2—2 of FIG. 1;

FIG. 3 is an enlarged transverse sectional view as seen generally along the Lines 3—3 of FIG. 2;

FIG. 4 is a bottom view of the tool seen in FIG. 1;

FIG. 5 is a top view of the tool seen in FIG. 1;

FIG. 6 depicts the tool seen in FIGS. 1–5 as mounted in the chuck of a conventional high speed dental drill and illustrates the use of the cutting tool in shaping the stump of a tooth in an overcrowded mouth area; and FIG. 7 is an enlarged view of a fragment of the tooth and tool seen in FIG. 6, but as seen during the preparation of the below gum line ledge on the tooth stump.

DETAILED DESCRIPTION OF THE INVENTION

Reference is first made to the drawings and more particularly to FIGS. 1–5. A cutting tool embodying the principles of the invention is therein designated to 10. It includes an elongated shaft 11 with opposite ends 12 and 13. The tool has a frustoconically shaped rigid body member 14 that has an axis of symmetry 15. Body 14 is arranged in the assembled tool with its axis of symmetry 15 coaxial to the longitudinal axis of the shaft, and is fixed to the lower end 13 of the shaft as seen in the drawings.

The shaft 11 and body member 14 are preferably made of stainless steel or other suitable metal. The body 14 has a disk-like top wall 16 with a center aperture 17 in which the shaft end 13 is received and fixed to the body. Around the aperture 17 for the shaft end 13 the wall 16 has an increased thickness dimension that provides a reinforcing hub 18 as seen in the drawings. The body member 14 also has a frustoconically shaped lateral wall 19 which converges upwardly and is integrally joined to the top wall 16 at the perimeter 20 of the wall 16.

The top wall 16, in the embodiment shown, has a circular interior planar surface 22 and the lateral body wall 19 has a frustoconically shaped interior lateral wall surface 23. These interior body surfaces 22 and 23 merge in the body interior and therein define a frustoconical interior hollow area or cavity 24 which has a circular opening 25 to the body exterior at the base end 26 of the body.

The lateral body wall 19 is of uniform thickness in the embodiment illustrated and has a frustoconical exterior lateral wall surface 27 which extends between the top wall 16 and base end 26 of the tool body. This surface 27 is symmetrical to, and preferably converges upon, the body axis 15 at an angular incline in a plane common to the axis, of between 17° and 24° as designated by the arrow 29.

The base end 26 of the body wall 19 is axially offset from the shaft end 13 and lies in a plane normal to the body axis 15. This arrangement provides an annular exterior base end surface 28 that surrounds the base end cavity opening 25 to the body exterior. This annular surface 28 and the exterior lateral wall surface 27 merge along a circular edge designated at 30.

Exterior surface 28, as well as interior surfaces 22 and 23, are covered with abrasive matter 31, such as diamond dust, Carborundum or other suitable abrasive material, that is suitably secured to the interior surfaces by conventional means well known in the art. The exterior surface 27 has a narrow continuous coating 32 of water repelling synthetic polymeric material and which is adhered to the surface along the circular edge 30 at the juncture of surfaces 27 and 28. The coating material may be any suitable water repelling polymeric material and is preferably one generally considered to have a low coefficient of friction, such as a polymeric derivative of one of the polyfluoroethylene or methylsiloxanes polymerics. The polymeric material known as TEFLON is admirably suited for use as the coating.

The lateral wall 19 has a plurality of passageways 33 that are circumferentially spaced apart and located between the top wall 16 and base end 26 of the body. These passageways 33 interconnect the body cavity 24 and body exterior and are illustrated in the preferred form of defining elongated slots or openings 34 that are so-arranged that the longitudinal axes 35 of each slot falls in a plane common to the body axis 15.

The illustrated cutting tool 10 is designed for rotation in a predetermined direction illustrated by arrow 36 during use, and the trailing side edge 37 that defines each slot has a wall surface 38 that is inclined so that fluids entering the slot are deflected by the surface 38 into the cavity 24 as the tool is rotated in the direction of arrow 36.

Reference is now made to FIGS. 6 and 7 and wherein the cutting tool is illustrated as being used in preparing a tooth stump for a crown. In FIG. 6, the tool 10 is seen as mounted in the chuck 44 of a conventional high speed dental drill 45. As thus mounted, the shaft 11 is received in the chuck 44 and the chuck is power driven to rotate the tool about the body axis 15 and in the predetermined direction indicated by arrow 36. The drill has a fluid conduit 46 that is connected to a pressurized source of water and/or air used for cooling purposes and the outlet 47 is aligned with a rotational path of movement of the body passageways 33 as will be more fully discussed below.

FIG. 6 illustrates one of the problems encountered by dentists in preparing a tooth stump and further illustrates certain advantages to the tool structure. Thus, the tooth to be prepared for the crown is designated at 48 and is seen in the close proximity to the adjacent teeth 49 and 50, that exist in the usual oral cavities. This close proximity of the teeth in the mouth area has heretofore dictated the need for using several different types of tools in the preparation of the tooth stump in order to avoid damage to the adjacent teeth.

The broken lines 51 illustrate the desired shape of the tooth stump after its preparation and with the spike being designated at 52 and the below gum line ledge being designated at 53. It will be apparent that a dentist using the cutting tool contemplated by the inventive concept will be provided with a wide selection of tools having various different diameters and heights and that the dentist will select a tool having the desired heighth and a diameter which will enable the tool to just fit in the space between teeth 49 and 50.

By virtue of the frustoconical shape of the tool body 14, and tool 10 can be manipulated to an off axis arrangement with respect to the tooth axis as seen in FIG. 6, and the abrasive nature of the annular surface 28 can be used for initially cutting the tooth in the crown area adjacent tooth 50. A typical initial arcuate cut of the kind contemplated is illustrated by the dotted line 54. During this cut 54, the abrasive matter 31 on surface 25 will serve to abrade away the enamel of the tooth, and the narrow coating 32 on the exterior surface 27 serves to protect the enamel on the adjacent tooth 50 from damage. Following the initial cut 54, the dentist then manipulates the assembly to another off axis position and makes another cut, designated at 55, in the immediate proximity of the other adjacent tooth 49. These initial arcuate cuts may vary in depths of penetration but are usually deep enough to expose a definite space between the tooth being prepared and the adjacent tooth because of the natural tooth taper. The frusto-conical shape of the exterior surface 27 of wall 19 greatly facilitates the making of these initial cuts 54 and 55 without damage to the adjacent teeth 49 and 50, and it has generally been found that such initial cuts, with practically all crowded teeth situations, can be handled if the incline of the surface 27 to the body axis 15 is between 17° and 24° as indicated by the arrow 29.

Following the initial cuts, the assembly is manipulated to a coaxial position with respect to the tooth axis, and the spike and ledge are formed by simply forcing the tool downwardly until the desired gum penetration is obtained. During this part of the process, the lateral sides of the spike are shaped and formed by the abrasive matter on the interior surface 23 of the lateral wall 19. During the end stages of the process, the top 56 of the spike is ground down by the abrasive matter on the interior surface 22 of the top wall 16 so that the entire spike is formed and shaped in accord with the contour of the body cavity 24.

The narrow coating 32 and abrasive nature of the annular surface 28 also perform important functions as the gum line is penetrated during use of the tool. The high speeds encountered with conventional dental drills permit the gum in the immediate proximity of the tooth 48 to be cleanly and rapidly abraded away as the base end of the body penetrates the gum area. Simultaneously, the water repellent nature of the coating 32 material provides a smooth surface, which by virtue of its water repellent nature, tends to repel the gum tissue and minimize the severity of the lesions. It is believed that the tissue abraded away at the base end of the cavity migrates to the cylindrical break 57 in the gum line (FIG. 7) as the tool penetrates the gum, and that the gum tissue and coating are separated by a thin tissue protecting film of fluid and abraded gum tissue and which minimizes any great amount of gum penetrating tissue damage along the break 57.

One of the problems encountered by the inventor in designing a tool of the nature contemplated herein was that of dissipating the heat generated during the abrasive process. Conventional means of projecting water and air onto the work surfaces of the tooth through the use of conventional lateral wall apertures to permit the fluids to enter the cavity were found to be less than satisfactory. The high lateral wall speeds encountered in using modern dental drills were found to be so great that water droplets projected into the lateral wall apertures encountered the body surface at the trailing edge of the aperture and were then broken up into a fine mist that was projected radially of the tool under the centrifugal forces involved. This mist had a tendency to obstruct the dentist's view of the work area and also raised the problem of confining the fluids to the oral cavity area. Thought was given to using a solid lateral wall and providing apertures in the top wall of the body with suitable shielding in a manner similar to that shown in Costoff U.S. Pat. No. 2,707,239. The thought however was rejected because the work area would then be completely obscured from the view of the dentist.

It was found that by providing an inclined edge 37 at the trailing side of the wall openings 34 water droplets projected into the opening 34 were projected inwardly into the cavity upon contact with the edge during the rotational movement of the tool, and that the objectionable mist problem was effectively resolved. It was additionally found that this type trailing edge arrangement in the lateral walls tended to confine the water to the cavity area once it entered the area, and that, in conjunction with the basically diverging nature of the cavity, the water entering the body cavity tended to advantageously migrate toward the cavity opening 25 and from which the water and debris were discharged to the body exterior.

In practice, the general shape of the lateral wall openings makes little difference in solving the cooling problem so long as the trailing edges of the openings are inclined in a manner that causes the water to be projected into the cavity areas as the tool rotates. Thus, the general shape of the openings may be circular, or rectangular, or any other suitable shape. However, to provide the greatest exposure of the work surface to the dentist's view, it is preferable that the shape of the passageways be such as to provide elongated slot-like openings 34 and in an arrangement where the longitudinal axes 35 of each opening falls in a plane common to the body axis. This type arrangement has been found to provide the greatest work area exposure to the dentist as the tool rotates.

The entire lateral surface 27 of the wall 19 may be coated with water repellent material to avoid damage to adjacent teeth if desired. It has been found preferable however, to limit the coating to the proximity of the circular edge 30 at the base of the tool since the coefficient of heat transfer of the coatings tends to retard heat dissipation through water contact with the peripheral surface.

From the foregoing disclosure it will be apparent that the inventor has provided a cutting tool which can be effectively used to shape both the spike and ledge of a tooth stump without the need for replacement of the cutting tool with other grinding equipment. It is also apparent that an effective means has been provided for coating the work surface in the body of a hollow grinding tool.

While only certan preferred embodiments of this invention have been shown and described by way of illustration, many modifications will occur to those skilled in the art and it is, therefore, desired that it be understood that it is intended herein to cover all such modifications as fall within the true spirit and scope of this invention.

What is claimed as new and what it is desired to secure by Letters Patent of the United States is:

1. A rotary cutting tool for use in preparing a tooth stump for the mounting of a tooth crown thereon, said tool comprising an elongated shaft adapted for reception in a power driven dental drill chuck and for rotation about its longitudinal axis, said shaft having opposite ends, a rigid body having an axis of symmetry and being fixed to the shaft in coaxial arrangement with the longitudinal axis at one of said ends, said body having a base end axially offset from said one of said ends, and joined top and lateral walls with interior surfaces that define a frustoconical interior cavity with an opening to the body exterior at said base end, said lateral wall having an annular exterior surface that surrounds said opening at said base end, and said body having abrasive matter secured to the interior surfaces of the top and lateral walls and to said annular exterior surface.

2. A rotary cutting tool in accord with claim 1 wherein said lateral wall has a frustoconical exterior surface that extends between the top wall and base end of said body.

3. A rotary cutting tool in accord with claim 2 wherein said frustoconical exterior surface is inclined to the body axis of symmetry at an angle between 27° and 24°.

4. A rotary cutting tool in accord with claim 2 wherein said body has water repelling synthetic material adhering to said frustoconical exterior surface.

5. A rotary cutting tool in accord with claim 4 wherein said water repelling synthetic material is selected from the group consisting of polyfluoroethylene derivatives and methylsiloxane derivatives.

6. A rotary cutting tool in accord with claim 4 wherein said frustoconical exterior surface and said annular exterior surface merge along a circular edge, and wherein said body has a continuous coating of water repelling synthetic material adhering to said frustoconical exterior surface along said circular edge.

7. A rotary cutting tool in accord with claim 1 wherein said lateral wall has a plurality of circumferentially spaced passageways which interconnect the body cavity and body exterior between the top wall and base end of the body.

8. A rotary cutting tool in accord with claim 7 wherein said tool has a predetermined direction of rotation about the axis of symmetry during the use thereof, wherein each of said passageways has a trailing side edge wall surface that is inclined and arranged to deflect fluids which enter the passageway into said cavity when said tool is rotated in said predetermined direction.

9. A rotary cutting tool in accord with claim 1 wherein said lateral wall has a frustoconical exterior surface that extends between the top wall and base end of said body and is inclined to the body axis of symmetry at an angle between 17° and 24°, and wherein said lateral wall has a plurality of circumferentially spaced passageways which interconnect the body cavity and the body exterior between the top wall and base end of the body.

10. A rotary cutting tool in accord with claim 9 wherein said frustoconical exterior surface and said annular exterior surface merge along a circular edge, wherein said body has a continuous coating of water repelling synthetic material adhering to said frustoconical exterior surface along said circular edge, wherein said tool has a predetermined direction of rotation about the axis of symmetry during use, and wherein each of said passageways has a trailing side edge wall surface that is inclined and arranged to deflect fluids which enter the passageway into said cavity when said tool is rotated in said predetermined direction.

11. A rotary cutting tool in accord with claim 1 wherein said lateral wall has an exterior lateral surface wherein said body has water repelling synthetic polymeric material adhering to the exterior lateral surface.

12. A rotary cutting tool in accord with claim 11 wherein said lateral wall has a plurality of circumferentially spaced passageways which interconnect the body cavity and body exterior between the top wall and base end of the body, wherein said tool has a predetermined direction of rotation about the axis of symmetry during the use thereof, wherein each of said passageways has a trailing side edge wall surface that is inclined and arranged to deflect fluids which enter the passageway into said cavity when said tool is rotated in said predetermined direction.

13. The combination with a dental drill having a power driven chuck adapted to receive and rotate a dental cutting tool in a predetermined direction, of a rotary cutting tool comprising an elongated shaft received in said chuck for rotation about its longitudinal axis, said shaft having opposite ends, a rigid body having an axis of symmetry and being arranged coaxially with said longitudinal axis, said body having a top wall fixed to the shaft at one of said opposite ends and having a perimeter, and a lateral wall joined to said top wall along said perimeter and having a base end that is offset from said one of said opposite ends, said top wall and lateral wall having interior surfaces that define a frustoconical interior cavity with an opening to the body exterior at said base end, said lateral wall having an annular exterior surface that surrounds said opening at said base end, and a plurality of circumferentially spaced passageways which interconnect the body cavity and body exterior between said top wall and said base end, said drill having fluid conduit means having a fluid outlet aligned with the path of rotational movement of the spaced passageways to project fluid thereinto, and said body having abrasive matter covering said interior surfaces of said top wall and lateral wall.

14. The combination in accord with claim 13 wherein said lateral wall has a frustoconical exterior surface which is inclined to the body axis of symmetry at an angle between 17° and 24°, wherein each of said passageways defines an elongated slot having an logitudinal axis that falls in a plane common to the axis of symmetry and has an inclined trailing side edge wall surface arranged to deflect fluids projected into said passageways from the fluid outlet into said cavity when said tool is rotatably driven in said predetermined direction.

15. The combination in accord with claim 14 wherein said frustoconical exterior surface and said annular exterior surface merge along a circular edge, and wherein said body has a narrow continuous coating of water repelling synthetic material adhering to said frustoconical exterior surface along said circular edge.

* * * * *

PO-1050
(5/69)

UNITED STATES PATENT OFFICE
CERTIFICATE OF CORRECTION

Patent No. 3,979,829          Dated October 14, 1976

Inventor(s) Albano Lemos

It is certified that error appears in the above-identified patent and that said Letters Patent are hereby corrected as shown below:

In column 4,
    line 65, cancel "and" and substitute -the-.

In column 6,
    line 3, cancel "2,707,239" and substitute -2,707,329-.

In column 7,
    line 15, cancel "27°" and substitute -17°-.

Signed and Sealed this

Fourteenth Day of December 1976

[SEAL]

Attest:

RUTH C. MASON
*Attesting Officer*

C. MARSHALL DANN
*Commissioner of Patents and Trademarks*